(12) United States Patent
Aiba

(10) Patent No.: US 7,540,900 B2
(45) Date of Patent: Jun. 2, 2009

(54) AIR CLARIFYING APPARATUS AND AIR CLARIFYING METHOD

(75) Inventor: Hideshige Aiba, Osaka (JP)

(73) Assignee: Aiba Co., Ltd., Osaka (JP)

( * ) Notice: Subject to any disclaimer, the term of this patent is extended or adjusted under 35 U.S.C. 154(b) by 260 days.

(21) Appl. No.: 10/568,843

(22) PCT Filed: Aug. 17, 2004

(86) PCT No.: PCT/JP2004/012047

§ 371 (c)(1),
(2), (4) Date: Sep. 18, 2006

(87) PCT Pub. No.: WO2005/018689

PCT Pub. Date: Mar. 3, 2005

(65) Prior Publication Data

US 2007/0022879 A1 Feb. 1, 2007

(30) Foreign Application Priority Data

Aug. 21, 2003 (JP) .............................. 2003-208146

(51) Int. Cl.
*B03C 3/013* (2006.01)

(52) U.S. Cl. .................... 95/3; 95/58; 96/19; 96/52; 96/63; 96/74; 96/223; 96/226; 422/4; 422/28; 422/124; 422/186.14

(58) Field of Classification Search ............ 95/2, 95/3, 58; 96/18, 19, 52, 63, 74, 223, 226; 422/186.07, 186.14, 186.15, 4, 28, 124
See application file for complete search history.

(56) References Cited

U.S. PATENT DOCUMENTS

| | | | | |
|---|---|---|---|---|
| 4,244,710 A | * | 1/1981 | Burger | ........................... 95/69 |
| 5,316,741 A | * | 5/1994 | Sewell et al. | ............ 422/186.21 |
| 5,667,563 A | * | 9/1997 | Silva, Jr. | ........................ 96/50 |
| 5,681,533 A | * | 10/1997 | Hiromi | ...................... 422/121 |
| 6,174,500 B1 | * | 1/2001 | Uno et al. | ............. 422/186.14 |
| 6,224,653 B1 | * | 5/2001 | Shvedchikov et al. | .......... 95/58 |

(Continued)

FOREIGN PATENT DOCUMENTS

JP        2000-5628       1/2000

(Continued)

OTHER PUBLICATIONS

Yasuhiro Tanimura et al., Bactericidal Effect of the Combined Gases of Negative Air Ions and Ozone, 1999, pp. 7-16, Antibacterial and Antifungal Agents, Japan.

(Continued)

*Primary Examiner*—Richard L Chiesa
(74) *Attorney, Agent, or Firm*—William L. Androlia; H. Henry Koda

(57) ABSTRACT

The air clarifying apparatus includes a negative ion generator and an indoor air circulator. It further includes an ozone generator having a capability of maintaining the average concentration value of ozone in an indoor atmosphere at 0.02 to 0.05 ppm, while the average concentration value of negative ions in the vicinity of the blowout port of the negative ion generator is maintained at 200,000 to 1,000,000 pieces/cc. With this configuration, the negative ions coexist with ozone having a low concentration.

4 Claims, 2 Drawing Sheets

U.S. PATENT DOCUMENTS

| | | | |
|---|---|---|---|
| 6,508,982 B1 * | 1/2003 | Shoji | 422/22 |
| 6,528,023 B2 * | 3/2003 | Fleischer | 422/186.04 |
| 6,843,835 B2 * | 1/2005 | Fornai et al. | 96/53 |
| 6,843,969 B1 * | 1/2005 | Anno | 422/186.04 |
| 7,368,003 B2 * | 5/2008 | Crapser et al. | 96/52 |
| 2002/0014401 A1 * | 2/2002 | Fleischer | 204/164 |
| 2003/0086813 A1 * | 5/2003 | Fleischer | 422/3 |

FOREIGN PATENT DOCUMENTS

| | | |
|---|---|---|
| JP | 2000-93836 | 4/2000 |
| JP | 2000-140688 | 5/2000 |
| JP | 2001-259470 | 9/2001 |
| JP | 2002-25747 | 1/2002 |
| JP | 2004-121811 | 4/2004 |

OTHER PUBLICATIONS

Tetsuo Watabe et al., Food Sterilization Technology Using Negative Air Ions and Ozone, 1998, pp. 17-21, CMP Japan, Japan.

* cited by examiner

AIR CLARIFYING APPARATUS AND AIR CLARIFYING METHOD

TECHNICAL FIELD

The present invention relates to an air clarifying apparatus and an air clarifying method in which negative ions and ozone are allowed to coexist at low concentrations.

BACKGROUND ART

An air clarifying apparatus is intended to maintain a comfortable indoor environment by carrying out air circulation using a fan while filtering dirty indoor air. In recent years, attention is paid to the effects of negative ions, such as an effect of making people refreshing, a blood purification effect, a mental stabilization effect and a fatigue recovery effect (these are hereafter generally referred to as a relaxation effect). Air clarifying apparatuses equipped with a negative ion generation function are being used widely. On the other hand, sterilizing apparatuses and bacteria elimination apparatuses that use the sterilizing effect of ozone are well known. However, the concentration of ozone that is used for this purpose is usually set to approximately 1% or more, for example, and this concentration is harmful to the human body. Hence, in air clarifying apparatuses, ozone has not been used positively for the purpose of sterilizing indoor air using the sterilizing effect of ozone or for an antibacterial purpose, in other words, for the purpose of suppressing bacterial growth, but rather has been eliminated as a harmful substance.

For example, Japanese Patent Application Laid-Open No. 2001-259470 discloses an example of an air clarifying apparatus in which ozone generated together with negative ions by high-voltage discharge is decomposed and eliminated using a catalyst. Japanese Patent Application Laid-Open No. 2000-140688 discloses examples of an air clarifying apparatus and an air-conditioning apparatus in which ozone generated secondarily together with negative ions by high-voltage discharge is used effectively for sterilization inside the apparatuses. In addition, Journal of the Society for Antibacterial and Antifungal Agents, Japan, Vol. 27, No. 11, p. 713 to 722 (hereafter referred to as paper 1) and Food processing and development (SHOKUHIN TO KAIHATSU), Vol. 33, No. 10, p. 17 to 21 (hereafter referred to as paper 2) disclose reports that discuss the effect of sterilization that is enhanced by the combined use of ozone and negative ions, but do not mention at all the coexistence of negative ions and ozone both having low concentrations not adversely affecting the human body and indoor equipment.

The present invention is achieved by taking a hint from the reports of the above-mentioned papers. More specifically, the present invention is intended to create a comfortable indoor environment by fully utilizing a relaxation effect obtained by negative ions and by allowing the negative ions to coexist with ozone so that the sterilizing effect or the antibacterial effect of an air clarifying apparatus is enhanced by the sterilizing power of the ozone.

DISCLOSURE OF THE INVENTION

For the purpose of attaining the above-mentioned object, an air clarifying apparatus according to the present invention is an air clarifying apparatus comprising a negative ion generating means and an indoor air circulating means, and further comprising an ozone generating means having a capability of maintaining the average concentration value of ozone being in a state of being discharged and scattered in a room at 0.02 to 0.05 ppm in an indoor atmosphere, and negative ions and the ozone having the above-mentioned concentration are allowed to coexist in an indoor atmosphere. In addition, an air clarifying method according to the present invention creates a comfortable indoor environment using the above-mentioned air clarifying apparatus and by circulating and stirring indoor air so that negative ions and the ozone having the above-mentioned concentration are allowed to coexist in an indoor atmosphere in an indoor atmosphere. When the concentration of ozone is in the above-mentioned range, adverse effects to the human body, such as a strong odor causing a headache for people living in the room, are not produced. A sterilizing effect or an antibacterial effect higher than that in the case that ozone is used independently is attained by the synergistic effect of ozone and negative ions as described later.

Furthermore, the relaxation effect of negative ions, such as an effect of making people refreshing, a blood purification effect, a mental stabilization effect and a fatigue recovery effect, can be attained, and a comfortable indoor environment can be created. Still further, because of the use of the negative ion generating means having a capability of maintaining the average concentration value of negative ions in the vicinity of the blowout port at 200,000 to 1,000,000 pieces/cc, adverse effects that may cause indoor equipment to fail are not produced, whereby it is possible to obtain an air clarifying apparatus suited for use in an environment where people live.

Negative ions disappear abruptly as they are away from the blowout port of the negative ion generating means, and the concentration thereof lowers. However, the amount of negative ions remaining in the relatively close vicinity of the blowout port is somewhat dependent on the amount generated using the negative ion generating means. If the concentration in the vicinity of the blowout port is more than 1,000,000 pieces/cc, dust is liable to attach to indoor equipment, more particularly, to electric circuit components and semiconductors, for example, thereby causing inconvenience, such as failures. If the concentration in the vicinity of the blowout port is less than 200,000 pieces/cc, the air flow has a lower chance of touching negative ions when passing through the negative ion generating means, and it is considered that the sterilizing effect or the antibacterial effect owing to the synergistic effect of ozone and negative ions is hardly obtained. For this reason, it is judged that a negative ion generating means having a capability of maintaining the average concentration value of negative ions in the vicinity of the blowout port thereof at 200,000 to 1,000,000 pieces/cc should desirably be used as the negative ion generating means in the air clarifying apparatus according to the present invention. It is thus possible to attain a desired effect by allowing negative ions and ozone to coexist at low concentrations not adversely affecting the human body and indoor equipment.

FIGS. 1 and 2 are graphs intended to support the above-mentioned judgment, showing the relationship between the concentration of ozone (on the horizontal axis) and sterilizing ratio (on the vertical axis) using the concentration of negative ions as a parameter. These graphs are formed on the basis of the data (mainly FIGS. 4, 5 and 6) disclosed in the above-mentioned paper 1. FIG. 1 relates to *staphylococcus aureus* and FIG. 2 relates to *escherichia coli*. Solid line A represents an ordinary air atmosphere (the concentration of negative ions thereof is assumed to be 150 to 200 pieces/cc), and solid line B represents an air atmosphere, the concentration of negative ions of which is 3,000,000 pieces/cc. Broken lines respectively represent air atmospheres having intermediate concentrations of 30,000 pieces/cc, 200,000 pieces/cc, 250,000 pieces/cc, 500,000 pieces/cc and 1,000,000 pieces/cc.

The lines other than the solid lines A and B, that is, the broken lines, are estimated lines because the data for only the ozone concentration of 0.03 ppm is disclosed in the paper 1.

As understood from these graphs, the sterilizing ratios indicated by the broken lines and the solid line B representing mixture gases obtained by positively adding negative ions are all higher than the sterilizing ratio indicated by the solid line A representing an ordinary air atmosphere to which negative ions are not added particularly and to which only ozone is added. In other words, it is found that the sterilizing effects of the mixture gases in which negative ions and ozone are allowed to coexist are more than several to ten times as high as the sterilizing effect obtained in the case that ozone is used independently only for conventional sterilization or bacteria elimination, even when the concentration of ozone is lower than the concentration of ozone used independently.

Hence, the inventor of the present invention paid attention to the low-concentration regions completely excluded from the targets in the above-mentioned paper and not adversely affecting the human body. First, with respect to negative ions, in the data of the paper, the concentration at which a sterilizing ratio of almost nearly 50% is obtained at 0.03 ppm, that is, 200,000 pieces/cc, was set as the lower limit, and the concentration not adversely affecting indoor equipment, that is, 1,000,000 pieces/cc, was set as the upper limit. Furthermore, with respect to ozone, the concentration at which no odor is detected and nobody has a headache, that is, 0.05 ppm, was set as the upper limit, and the concentration at which a sterilizing ratio of 30% or more is obtained at a negative ion concentration of 1,000,000 pieces/cc was set as the lower limit.

However, the sterilizing ratio differs depending on the type of bacteria. Furthermore, the above-mentioned paper is a report that discloses the results obtained when the samples of bacteria under test were placed inside a small chamber and then continuously subjected to an atmosphere containing negative ions and ozone having predetermined concentrations for a predetermined time. On the other hand, in the present invention, negative ions generated are scattered into an indoor atmosphere, and the concentration thereof lowers. Hence, it is considered that the acceleration of the sterilizing effect or the antibacterial effect attained when the air flow touches negative ions having a relatively high concentration occurs only for a short time during which the air flow containing ozone passes through the negative ion generating means and then is discharged. Therefore, this condition differs from the condition in the paper in which the concentrations are maintained at predetermined values at all times. Hence, the data of the paper cannot be applied directly to the present invention as a matter of course.

FIG. 3 is a graph exemplifying the relationship between the distance from the blowout port and the concentration of negative ions. An experiment was carried out as described below. A wooden base having a height of 85 cm was placed at the center of a workshop, the size of the floor of which was 4 m by 15 m, and the height of which to the ceiling was 3 m. On the wooden base, a negative ion generator having a flow rate of 1.4 m$^3$/minute was placed, air was blown out in the horizontal direction, and the concentration of negative ions was measured using a measuring instrument (ICT-201A made by ANDES Electric Co., Ltd.) that was placed at the same height. FIG. 3 shows that the concentration of negative ions, 1,000,000 pieces/cc at a position 10 cm away from the blowout port, lowers abruptly as the distance from the blowout port increases.

As described above, the concentration of negative ions in an indoor atmosphere lowers abruptly at positions away from the blowout port. In addition, the capability of the negative ion generating means, that is, the amount of ions generated changes depending on not only the concentration in the vicinity of the blowout port but also the flow rate, velocity, etc. of the air flow. The concentration in the indoor atmosphere is also different depending on the size of a room in which the air clarifying apparatus is installed. However, the concentration of negative ions in the air flow at the time when the air flow was sucked into the negative ion generator after circulation around a room and returning to the air clarifying apparatus was approximately 700 pieces/cc, provided that the concentration in the vicinity of the blowout port was in the range of 200,000 to 1,000,000 pieces/cc, regardless of the flow rate and the size of the room. Hence, it is considered that the concentration of negative ions at an indoor position somewhat away from the generating means is approximately 700 pieces/cc, and that the concentration is in a stable state. This concentration value is approximately three times as high as the value in suburbs and is almost the same value in mountainous areas, thereby being a value at which the relaxation effect can be obtained sufficiently.

The above-mentioned paper 1 explains that it is considered that when negative ions and ozone are allowed to coexist, they react with each other, a third substance is generated, and the third substance has a sterilizing effect. In the apparatus according to the present invention, when the air flow containing ozone passes through the negative ion generating means as described above, the air flow touches negative ions having a relatively high concentration, whereby the sterilizing effect or the antibacterial effect is accelerated. In addition to the acceleration, the sterilizing effect or the antibacterial effect of the above-mentioned third substance is maintained in an indoor atmosphere in which the concentration of negative ions is stabilized at approximately 700 pieces/cc, because the concentration is hardly affected by the difference in concentration in the vicinity of the blowout port. It is thus estimated that the sterilizing effect or the antibacterial effect is attained collectively by these factors.

As described above, the data of the paper cannot be applied directly. Furthermore, even in the low-concentration regions completely excluded from the targets in the paper, that is, the concentration of negative ions in the range of 200,000 to 1,000,000 pieces/cc in the vicinity of the blowout port and the concentration of ozone in the range of 0.02 to 0.05 ppm, it is considered that a sufficient sterilizing effect or a sufficient antibacterial effect can be obtained, provided that indoor air is circulated and stirred using the apparatus and the method according to the present invention.

BEST MODES FOR CARRYING OUT THE INVENTION

An embodiment according to the present invention will be described below.

Figure 1:
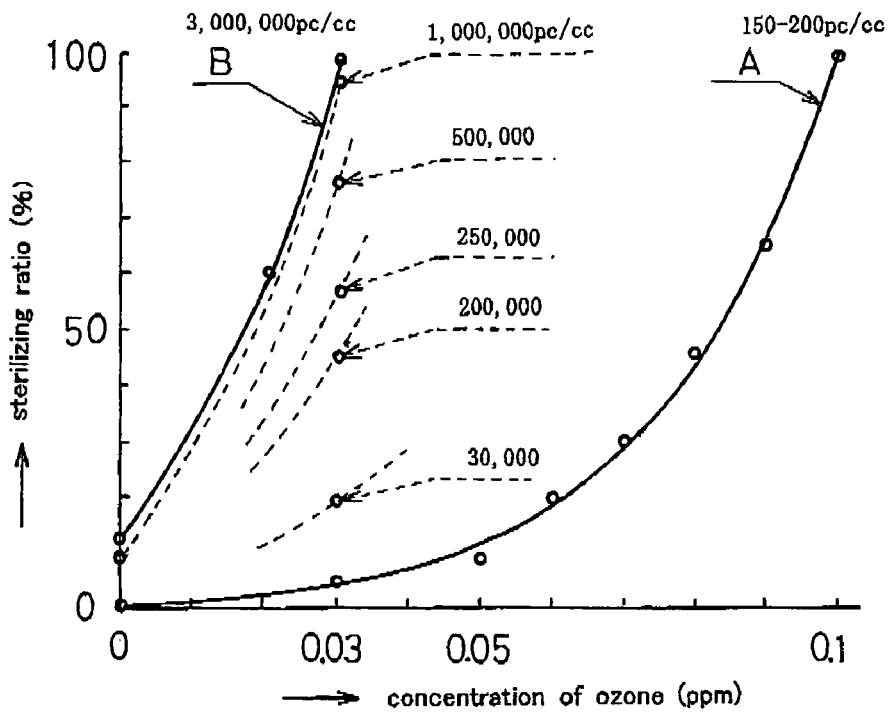
FIG. 1 is a graph showing the relationship among the concentration of ozone, sterilizing ratio and the concentration of negative ions.
Figure 2:
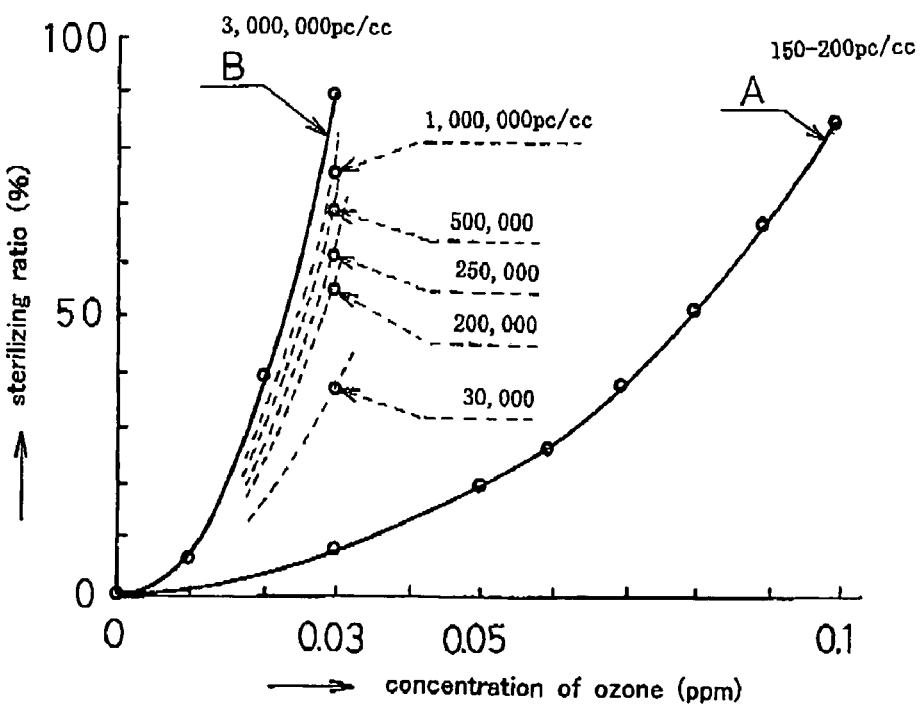
FIG. 2 is a graph showing the relationship among the concentration of ozone, sterilizing ratio and the concentration of negative ions, a graph similar to FIG. 1.
Figure 3:
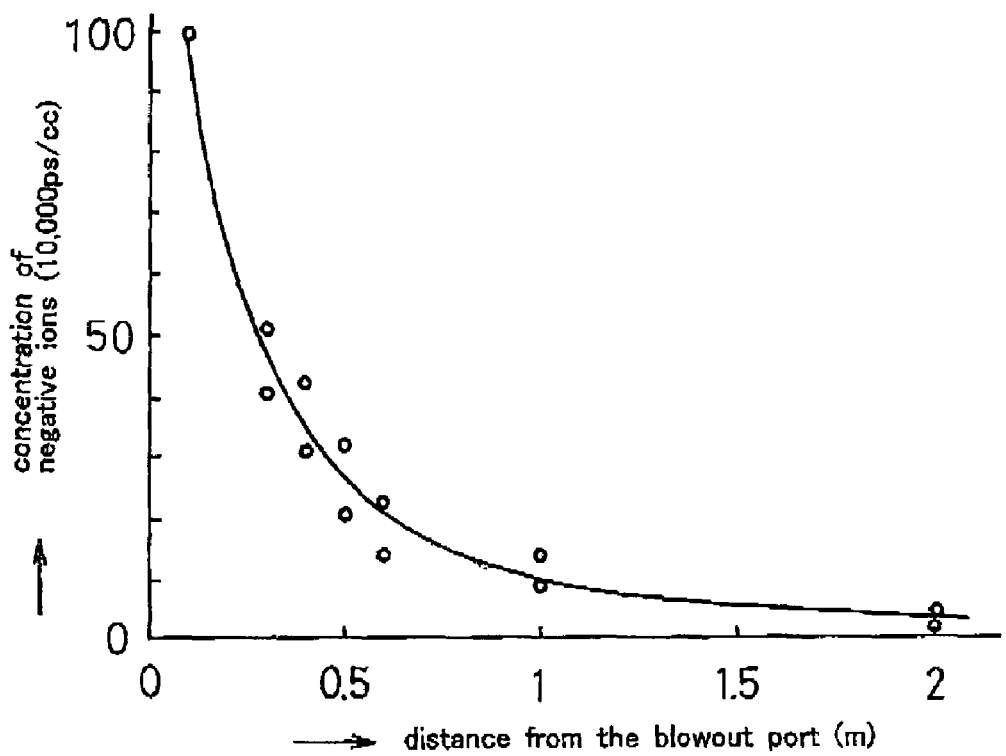
FIG. 3 is a graph showing the relationship between the distance from the blowout port and the concentration of negative ions.
Figure 4:
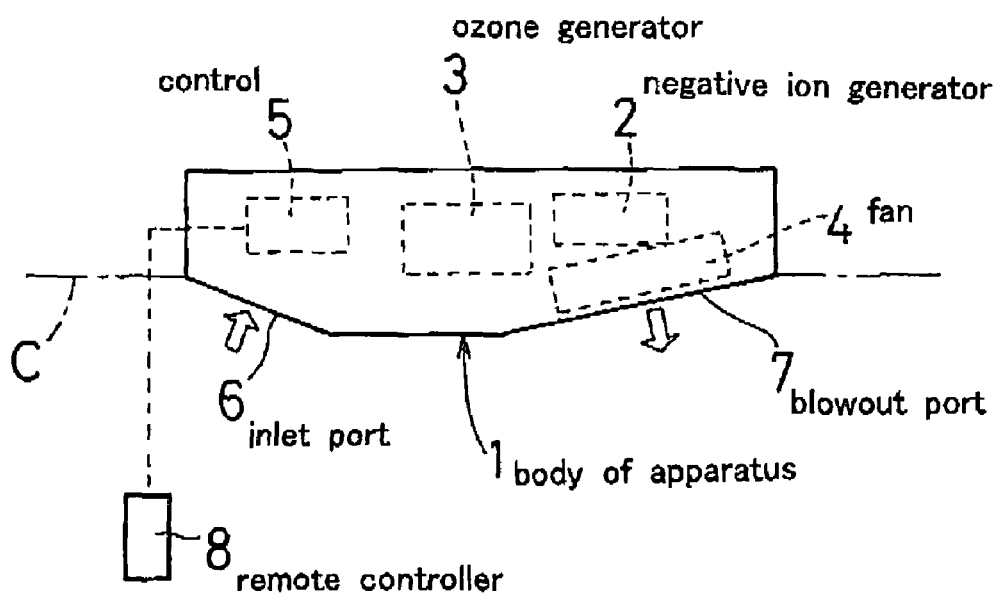
FIG. 4 is a view showing the configuration of an apparatus according to an embodiment of the present invention.

In FIG. 4, numeral 1 designates the body of an apparatus. The body 1 of the apparatus incorporates a negative ion generator 2 that generates negative ions, an ozone generator 3 that generates ozone, a fan 4, a control section 5 equipped with a CPU, a power supply section (not shown), etc., and has an inlet port 6 and a blowout port 7. In addition, numeral 8 designates a remote controller. The remote controller 8 is equipped with a main switch; an operation section for turning ON/OFF the negative ion generator 2, the ozone generator 3, the fan 4, etc.; a timer setting section; etc. as necessary. Furthermore, the remote controller 8 is also equipped with an air flow rate adjustment operation section because the generated amounts of negative ions and ozone are changed depending on the air flow rates at the generators. Although filters are provided at appropriate positions in the air flow passage from the inlet port 6 to the blowout port 7, they are not shown in the figure.

The structure and shape of the body 1 of the apparatus are similar to those of the indoor unit of an air conditioner. The negative ions and ozone generated from the apparatus are discharged together with the air taken from the inlet port 6 from the blowout port 7 into the room using the fan 4. The fan 4 is used not only for blowing but also for air stirring. However, if its capability for uniformly distributing ions and ozone is insufficient, auxiliary fans may also be provided separately. The apparatus shown in the figure is an example of a type that is installed on the ceiling, and letter C designates a ceiling surface.

As the negative ion generator 2, and the ozone generator 3, those having well-known structures can be used as necessary. In FIG. 4, the negative ion generator 2 and the ozone generator 3 are shown separately. However, for example, in the case of a generator that simultaneously generates negative ions and ozone by corona discharge, the generator has a structure in which both generators are integrated. In this embodiment, a negative ion generator capable of discharging negative ions amounting to the range of 200,000 to 1,000,000 pieces/cc at a flow rate of 1.4 $m^3$/minute is used as the negative ion generator 2, and an ozone generator capable of generating ozone amounting to 20 to 30 mg/h is used as the ozone generator 3. However, in the case that the room is large, multiple units of the body 1 of the apparatus should be installed, and they should only be used properly depending on circumstances so that they can be controlled collectively or individually, for example.

At the time of the operation of this apparatus, after the apparatus is operated continuously until the concentrations of negative ions and ozone reach desired steady-state values, a necessary operation time period is calculated according to the size of the room in which the apparatus is installed, the capabilities of the negative ion generator 2 and the ozone generator 3, the flow rate of the fan 4, the disappearance rates of ions and ozone, etc. Then, setting is carried out so that the necessary operation time period is obtained and so that the negative ion generator 2 and the ozone generator 3 are operated intermittently or continuously as necessary. This setting should only be programmed in advance according to the installation environment of the apparatus, for example. In this case, the remote controller 8 should be configured so as to be consistent with the specification in which the advance setting can be carried out. Because negative ions, in particular, disappear abruptly after discharge and the concentration thereof is stabilized to a nearly constant value as described above, even if the negative ion generator 2 is operated continuously, it is considered that no problem occurs from a practical standpoint.

When it is necessary to maintain the concentration of negative ions and the concentration of ozone at constant values, it may also be possible that sensors for detecting the respective concentrations are installed, that the results of the detection are fed back, and that the operation states of the negative ion generator 2, the ozone generator 3 and the fan 4 are controlled according to the results, without using the above-mentioned calculation.

The air clarifying apparatus according to the present invention has the above-mentioned configuration. When the apparatus is operated, negative ions and ozone are discharged into the room. Simultaneously with the relaxation effect of the negative ions, the sterilizing effect or the antibacterial effect of the third substance generated by the synergistic effect of negative ions and ozone is attained in addition to the effect of ozone itself, although the concentration of ozone is lower than the concentration of ozone used independently and although the concentration is low enough not to adversely affect the human body. Furthermore, the indoor air is stirred while being circulated using the fan 4. As a result, a comfortable indoor environment can be created. When the decaying states of several kinds of foods placed in the living room of an ordinary house in the case that the apparatus according to the present invention was operated were compared with those in the case that the apparatus was not operated, the number of days to decay was increased in the case that the apparatus according to the present invention was operated, although such scholarly precise experiments as those reported in the papers 1 and 2 were not be able to be carried out. Consequently, it was possible to confirm the effect of the present invention.

The way people feel about the relaxation effect varies greatly in individuals. In addition, negative ions are apt to disappear easily. It is sometimes difficult to uniformly distribute negative ions and ozone in actual practice. Furthermore, variations are apt to occur in the measured concentrations of negative ions and ozone depending on measurement instruments and measurement conditions. It is thus desirable that the above-mentioned values are not precise values but are assumed to be approximate guideline values.

INDUSTRIAL APPLICABILITY

The present invention is particularly suited for air clarification in houses, offices, relatively small workshops and the like.

The invention claimed is:

1. An air clarifying apparatus (1) comprising negative ion generating means (2) for maintaining an average concentration value of negative ions in the vicinity of a blowout port thereof at 200,000 to 1,000,000 pieces/cc and indoor air circulating means (4), and further comprising ozone generating means (3) for maintaining the an average concentration value of ozone being in a state of being discharged and scattered in a room at a range of 0.02 to 0.05 ppm in an indoor atmosphere, wherein the negative ions and ozone having said concentration are allowed to coexist in an indoor atmosphere.

2. The air clarifying apparatus according to claim 1 comprising a means for controlling said negative ion generating means such that said average concentration of negative ions is set at a predetermined value within said range of 200,000 to 1,000,000 pieces/cc and for controlling said ozone generating means such that said average concentration of ozone is set at a predetermined value within said range of 0.02 to 0.05 ppm.

3. An air clarifying method for creating a comfortable indoor environment using an air clarifying apparatus (1) comprising a negative ion generating means (2) for maintaining an average concentration value of negative ions in the vicinity of a blowout port at 200,000 to 1,000,000 pieces/cc, an indoor air circulating means (4) and an ozone generating means (3) for maintaining an average concentration value of ozone being in a state of being discharged and scattered in a room at a range of 0.02 to 0.05 ppm in an indoor atmosphere, and by circulating and stirring indoor air so that the negative ions and the ozone having said concentration are allowed to coexist in an indoor atmosphere.

4. The air clarifying method according to claim 3 comprising a means for controlling said negative ion generating means such that said average concentration of negative ions is set at a predetermined value within said range of 200,000 to 1,000,000 pieces/cc and for controlling said ozone generating means such that said average concentration of ozone is set at a predetermined value within said range of 0.02 to 0.05 ppm.

* * * * *